United States Patent [19]

Burov et al.

[11]  4,228,153
[45]  Oct. 14, 1980

[54] COSMETIC COMPOSITION

[75] Inventors: Pencho V. Burov, Dryanovo; Nadejda A. Kyuleva, Sofia, both of, Bulgaria

[73] Assignee: DSO "Pharmachim", Sofia, Bulgaria

[21] Appl. No.: 914,506

[22] Filed: Jun. 12, 1978

[30] Foreign Application Priority Data

Jun. 10, 1977 [BG] Bulgaria .................................. 36563

[51] Int. Cl.$^2$ ..................... A61K 35/12; A61K 35/56; A61K 31/675
[52] U.S. Cl. ...................................... 424/95; 424/177; 424/200; 424/359

[58] Field of Search .................. 424/177, 95, 359, 200

[56] References Cited

U.S. PATENT DOCUMENTS

| 3,839,590 | 10/1974 | Battuta ................................. 424/359 |
| 3,941,722 | 3/1976 | Shevlin ............................. 424/359 X |
| 3,949,073 | 4/1976 | Daniels et al. ....................... 424/177 |
| 3,991,184 | 11/1976 | Kludas et al. ....................... 424/177 |

*Primary Examiner*—Leonard Schenkman

[57] ABSTRACT

A novel cosmetic is obtained by mechanical mixing of a 0.6–0.8% solution of a collagen and adding thereto from 0.6–1% of pyridoxal phosphate.

2 Claims, No Drawings

COSMETIC COMPOSITION

This invention relates to a method for the preparation of a cosmetic composition and to the cosmetic so obtained. More particularly, the present invention relates to a method for the preparation of a cosmetic composition upon a collagen base and to the resultant cosmetic.

Heretofore, cosmetics have been prepared which comprise a collagen alone or in combination with vitamins K, E, and F. The prime purpose of such cosmetics is to compensate for the loss of soluble collagens occasioned either by artificial or natural ageing of human skin. This end is obtained by direct penetration of the cosmetic into the skin and ultimately the amino acids are absorbed into the human skin by osmosis. These cosmetics tend to enhance the elasticity and the external appearance of the skin without causing added fibrillation. The process of absorption, however, is very slow and is dependent upon the extent to which fatty tissue covering the pores in the skin is removed.

In accordance with the present invention, the limitations of the prior art cosmetics alluded to are effectively obviated by the use of a system comprising collagen co-enzyme wherein the collagen is an amino acid donor and the co-enzyme enters into the metabolism of the connective tissue. As a result of the foregoing mechanism, a substantial enhancement in elasticity, outer appearance, and fibrillation of the skin is achieved in comparison with the noted prior art cosmetics. Briefly, the novel cosmetic described herein comprises a mixture of a solution of a water-soluble collagen containing pyridoxal-5-phosphate.

A method for preparing the cosmetic of the invention follows:

The first step in preparing the novel cosmetic involves mechanically mixing an aqueous solution of a water-soluble collagen having a concentration ranging from 0.6–0.8%, by volume. The solution temperature is maintained within the range of 20°–30° C. and mixing effected while successively adding nypagin, sorbic acid, and ethyl alcohol. After a time period ranging from 15–20 minutes, the mixer is stopped and from 0.6–1%, by weight, pyridoxal-5-phosphate is added thereto in small quantities. The resultant product is then poured into dark bottles or opaque vessels and stored at a temperature ranging from 0°–25° C.

The main advantage of the cosmetic so obtained is that there is rapid inclusion of the collagen in the metabolism of the connective tissue and the effect upon the skin is quickly manifested organoleptically in terms of improved turgur, external appearance, and uniformity.

Examples of the present invention are set forth below. It will be appreciated by those skilled in the art that the examples are for purposes of exposition only and are not to be construed as limiting.

EXAMPLE I

This example describes the preparation of pyridoxal-5-phosphate from pyridoxamine, a derivative of vitamin $B_6$. Into a 10-liter glass reactor adapted with a serpentine electric heater and a mechanical agitator 2.5 kg of pyridoxamine dichlorinehydrate was placed. A mixture comprising 4 liters of orthophosphoric acid and 500 grams of biphosphor pentoxide was placed in the reactor and the mixture heated to a temperature ranging from 60°–70° C. while agitating at a rate ranging from 40–50 rpm. Mixing was continued for 1 hour and the resultant mixture was cooled without agitation to a temperature ranging from 20°–25° C. Then, 400 grams of manganese dioxide was added and agitation again initiated at a temperature ranging from 30°–35° C., the reaction continuing for 30 minutes. Following, the mixture was cooled and 300 grams of active charcoal added in order to absorb cathions in the liquid. The mixture was next filtered and the resultant filtrate treated with 200 ml of acetone. Following mixing, the pyridoxal-5-phosphate sinks as a sediment, the liquid phase being siphoned off and the sediment dried at room temperature.

EXAMPLE II

This example describes the preparation of a collagen. Five liters of a 1% solution of a soluble collagen, obtained in accordance with the procedure described in Bulgarian Authorship Certificate 29435, was passed through a jet colloid mill and filtered through a filter press with charges. The procedure set forth in the Bulgarian Authorship Certificate is as follows:

Mill 2 kg of limed fur middle layer in a meat-chopper. Neutralize the obtained mixture to pH-7 with ammonium chloride. Wash thoroughly with running water at 20° C. so that the obtained salts are extracted. Place 5 l of borate buffer pH-9.5 in a glass reactor (simex) equipped with a stirrer and a jacket with a contact thermometer to regulate the temperature. In the same reactor place the above obtained mass. To this dispersion add 5 g enzyme alcaline protease B-72 and 5 g sodium silifluoride as an antiseptic agent. Adjust the temperature to 35°±2° C. with the help of the jacket thermoregulation. Turn the stirrer on 30 r/m for 10 hours. After the fixed period is over, discharge the mixture through a drain-cock. Then pour 10% solution of ammonium chloride out of a container for the purpose of extracting the enzyme from the furs. The extraction is considered completed when the sample of the washing waters does not show any absorption at 280 nm on the UV spectrophotometer. When the enzyme is extracted, turn on the running water and the stirrer. Remove the washing water through a drain-cock. Add 0.1 citric acid out of a container. Adjust again the temperature to 35° C., turn the stirrer and let the process continue for 6 hours. Discharge the obtained viscose solution by a drain-cock through a filtering cloth. Remove the solid particles from the reactor and wash with water. Place the filtrate in the reactor and neutralize to the isoelectric point of Collagen pH7 to 7.8. As a result snow-white tropo-collagen fibrils are reconstructed out of the solution. Discharge the liquid, wash the fibrils several times with water and transfer them in a mixer of 10.00 r/m. To 100 g Collagen fabrils add 50 ml 0.01 n citric acid and 50 ml isopropanol. Turn the mixer for 10 minutes only. The obtained mixture is of pH-3.2–4.5 and viscosity 5,000 c.p. This particular dispersion is included in the composition of face creams in a quantity of 5% to 15% depending on the purpose of the cream and shampoo. The resultant produce was almost clear and contained from 0.6–0.8% collagen in solution.

EXAMPLE III

This examples describes preparation of the cosmetic. Two liters of the solution of Example II were placed in a 5-liter glass reactor having a water jacket for cooling and a mixer. The temperature of the solution was maintained within the range of 20°–25° C. and the mixer activated. At this juncture, 6 grams of nypagin (methylp-hydroxybenzoate), 8 grams of sorbic acid, and 120 ml of 90% ethyl alcohol were successively added. After 20 minutes, mixing was stopped and 12 grams of the pyridoxal-5-phosphate of Example I added in small increments to the mixture. The product was then poured into storage vessels and stored at a temperature ranging from 0°–20° C.

What is claimed is:

1. A cosmetic composition including an active component comprising a mixture of a 0.6–0.8% solution of a collagen and from 0.6–1% pyridoxal-5-phosphate.

2. Composition in accordance with claim 1, further comprising methyl-p-hydroxybenzoate, sorbic acid, and ethyl alcohol.

* * * * *